United States Patent [19]

Shoesmith, deceased

[11] Patent Number: Plant 6,074

[45] Date of Patent: Dec. 29, 1987

[54] CHRYSANTHEMUM PLANT NAMED ATLANTIS

[75] Inventor: Leonard H. Shoesmith, deceased, late of Westfield, England, by May V. Shoesmith, executrix

[73] Assignee: Ball PanAm Plant Company, Parrish, Fla.

[21] Appl. No.: 815,002

[22] Filed: Dec. 31, 1985

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Atlantis having decorative capitulum type and flat capitulum form, pure white ray floret color, nine week flowering response, vigorous growth habit, medium plant height and upright branching pattern.

1 Drawing Figure

The present invention comprises a new and distinct cultivar of *Dentrenthema morifolium,* Ramat., previously *Chrysanthemum morifolium,* Ramat., hereinafter referred to by the cultivar name Atlantis.

Atlantis is a product of a planned breeding program which had the objective of creating new Chrysanthemum cultivars with decorative capitulum type, pure white ray floret color, and rapid flowering response from the start of short days. Such traits in combination were not present or needed improvement in previously available commerical cultivars.

Atlantis was originated from a hybridization made in a controlled breeding program by Leonard H. Shoesmith in Westfield, Woking, Great Britain in 1977. The male and female parents are unknown at this time.

Atlantis was discovered and selected as one flowering plant within the progeny of the stated parentage by or under the supervision of Leonard H. Shoesmith in November of 1978 in a controlled environment in West Chicago, Ill.

The first act of asexual reproduction of Atlantis was accomplished when vegetative cuttings were taken from the initial selection in February of 1979 in a controlled environment in West Chicago, Ill. by a technician working under formuations established and supervised by Leonard H. Shoesmith. Horticultural examination of selected units initiated December of 1979 has demonstrated that the combination of characteristics as herein disclosed for Atlantis are firmly fixed and are retained through successive generations of asexual reproduction.

Atlantis has not been observed under all possible environmental conditions. The phenotype may vary significantly with variations in environment such as temperature, light intensity and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Atlantis which in combination distinguish this Chrysanthemum as a new and distinct cultivar:

1. Decorative capitulum type.
2. Flat capitulum form.
3. Pure white ray floret color.
4. Diameter of 2–3" across face of capitulum.

5. Vigorous growth habit.
6. Nine (9) week flowering response.
7. Medium plant height of 250–300 mm. and upright branching pattern.

Of the many commercial cultivars known to the present inventor, the most similar in comparison to Atlantic is Powerhouse, disclosed in U.S. Plant Pat. No. 5,531. In comparison to Powerhouse, Atlantis has a much more vigorous growth rate, requiring more applications of B-9 and tall treatment in most Chrysanthemum programs. Atlantis also has thinner stems and a less compact growth habit than Powerhouse. The response time (nine weeks), flower type and form, and flower color of Atlantis are similar to those same characteristics of Powerhouse.

The accompanying photographic drawing shows typical inflorescence and foliage characteristics of Atlantis. The photograph is in black and white except where the flowers are colored, such color representing the true flower color of Atlantis.

In the following description, color references are made to The Royal Horticultural Society Colour Chart. The color values were determined at approximately 11:00 a.m. on Dec. 1, 1985 under florescent light at Parrish, Fla.

Classification:

*Botanical.*—*Denthenthema morifolium,* Ramat., cv Atlantis.

*Commercial.*—Disbud pot mum.

INFLORESCENCE

A. Capitulum:

*Form.*—Flat.

*Type.*—Decorative.

*Diameter across face.*—2"–3".

B. Corolla of ray florets:

*Color (general tonality from a distance of three meters).*—White.

*Color (upper surface).*—155D.

*Color (under surface).*—155D.

C. Corolla of disc florets:

*Color (mature).*—Insignificant.

*Color (immature).*—Insignificant.

D. Reproductive organs:

*Androecium.*—Insignificant.

*Gynoecium.*—Present in ray florets only; insignificant.

PLANT

A. General appearance:
*Height.*—Approximately 250–300 mm.

B. Foliage:
*Color (upper surface).*—147A.
*Color (under surface).*—147B.
*Shape.*—Deeply lobed and slightly serrated.

I claim:

1. A new and distinct cultivar of Chrysanthemum plant named Atlantis, as described and illustrated, and particularly characterized by its decorative capitulum type and flat capitulum form, pure white ray floret color, nine week flowering response, vigorous growth habit, medium plant height and upright branching pattern.

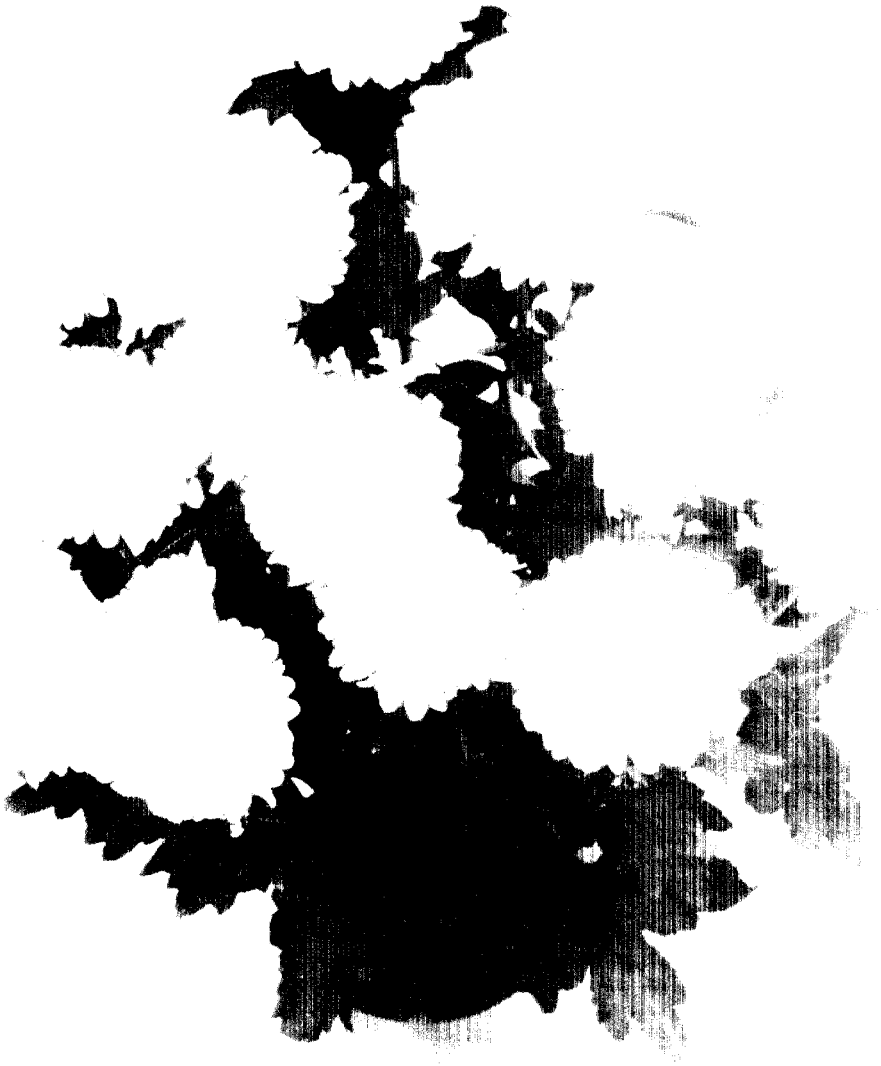

* * * * *